United States Patent
Takamatsu et al.

[11] Patent Number: 5,298,970
[45] Date of Patent: Mar. 29, 1994

[54] SAMPLE EVALUATING METHOD BY USING THERMAL EXPANSION DISPLACEMENT

[75] Inventors: Hiroyuki Takamatsu; Yoshiro Nishimoto, both of Kobe; Shingo Sumie, Kakogawa, all of Japan

[73] Assignee: Kabushiki Kaisha Kobe Seiko Sho, Kobe, Japan

[21] Appl. No.: 955,241

[22] Filed: Oct. 1, 1992

Related U.S. Application Data

[63] Continuation of Ser. No. 672,570, Mar. 20, 1991, abandoned.

[30] Foreign Application Priority Data

| Mar. 20, 1990 [JP] | Japan | 2-70968 |
| Mar. 20, 1990 [JP] | Japan | 2-70968 |
| Aug. 10, 1990 [JP] | Japan | 2-213052 |

[51] Int. Cl.⁵ ............... G01B 9/02
[52] U.S. Cl. ............... 356/349; 356/358; 356/360
[58] Field of Search ........... 356/349, 357, 358, 359, 356/360; 374/55

[56] References Cited

U.S. PATENT DOCUMENTS

| 3,409,369 | 11/1968 | Bickel | 356/349 |
| 4,752,140 | 6/1988 | Cielo et al. | 356/358 |
| 4,924,477 | 5/1990 | Gilmore et al. | 356/358 |
| 4,930,894 | 6/1990 | Baldwin | 356/349 |
| 4,948,251 | 8/1990 | Kondo | 356/349 |
| 4,989,980 | 2/1991 | Berg | 356/357 |

*Primary Examiner*—Samuel A. Turner
*Attorney, Agent, or Firm*—Oblon, Spivak, McClelland, Maier & Neustadt

[57] ABSTRACT

When evaluating defects, etc. of a sample by measuring thermal expansion displacement on the surface of the sample, which is produced by irradiating thereto an excitation beam of which intensity is cyclically modulated, a measuring beam having the displacement frequency $F_1$ is irradiated to the vibrating surface of the sample, and the reflection beam is interfered with a reference beam having the frequency $F_2$. The beat wave signal $E_1$ (Beat frequency $F_b = F_1 - F_2$) is converted to a binary signal $E_2$. Then, the sample is evaluated by signals which are obtained by giving a suitable processing to the binary signals. In addition, the optic axes alignment is eliminated by utilizing the excitation beam itself concurrently as measuring beam.

6 Claims, 9 Drawing Sheets

SAMPLE EVALUATING METHOD BY USING THERMAL EXPANSION DISPLACEMENT

This application is a Continuation of U.S. application Ser. No. 07/672,570, filed on Mar. 20, 1991, now abandoned.

BACKGROUND OF THE INVENTION

1. Field of the Invention

The present invention relates to a sample evaluating method for evaluating defects or the like of a sample by irradiating a cyclically intensity-modulated excitation beam to the sample and by measuring the thermal expansion displacement resulting therefrom on the surface of the sample.

2. Description of the Prior Art

In the case that an excitation beam which has been cyclically intensity-modulated is irradiated to a sample, the sample is heated by absorption of the excitation beam and is thermally expanded thereby. As the excitation beam and is cyclically intensity-modulated, the temperature changes of the sample on account of heating are made cyclic, thereby causing the sample to be thermally expanded and displaced. Such a method for evaluating a sample by measuring the thermal response has been known as the photoacoustic method.

FIG. 8 shows a method for measuring the thermal expansion displacement of a sample by use of the Michelson laser beam interference method (Miranda, Applied OPTICS Vol. 122, No. 18, P2882 (1983)). Herein, 61 indicates a sample to be measured, 62 indicates an excitation beam source to give thermal expansion displacement to the sample, and the beam which comes from the excitation beam source 62 is intensity-modulated by a chopper 63 and is irradiated to the sample 61. The thermal expansion displacement is metered by a laser interference method. Therefore, the beam coming from a measuring laser 64 is divided into two by a translucent mirror 65, one beam of which is irradiated to the point of thermal expansion measurement of a sample and the other of which is irradiated to a fixed mirror 66. Then, the reflection beam therefrom is interfered and is received by a photoelectric converter 67. The electric output E from the photoelectric converter 67 is arithmetically processed by an expression (1).

$$E = C_1 + C_2 \cos(P_{(t)} + \phi) \ldots \quad (1)$$

Here, C1, C2 and $\phi$ are constants which depend upon the composition of a sample 61 and an interferometer and upon photoelectric conversion coefficients, and $\lambda$ is the wavelength of a measuring laser. P(t) is a phase change by surface displacement of a sample due to thermal expansion displacement resulting from irradiation by the excitation beam, and the thermal expansion displacement of a sample is metered by this measurement, thereby causing the thermo-elastic characteristics thereof to be evaluated. FIG. 9 shows a method based on the reflectivity measuring method (Refer to the Japanese Pat. Laid-Open Gazette No. Sho-61-2046). The beam which comes from the excitation laser 30 is cyclically intensity-modulated by a modulator 32 and is irradiated to a sample 22, thereby causing the sample to cyclically produce temperature changes. The temperature changes cause changes in the optical reflectivity of the sample. In order to detect changes in the optical reflectivity, measuring laser 50 is irradiated to the temperature change measuring point of a sample (the same position as the point of excitation laser irradiation in this Figure) through a mirror 36, and the reflection beam thereof is detected by a photodetector 56. The change of reflectivity is obtained by a signal processing circuit 58 from this output.

In the method for measuring the thermal expansion of a sample by the former Michelson laser beam interference, changes of the constants $C_1$ and $C_2$ in the former expression (1) result in a lowering of the measurement accuracy as disturbance.

For instance, there are cases in which the reflectivity of a sample changes due to temperature changes of the sample caused by irradiation of an excitation beam and due to changes of the plasma (electrons, holes) density (in case of semiconductor sample). In this case, as signals of an interference beam include disturbance signals accompanying the changes of reflectivity, it is impossible to meter true thermal expansion signals from the signals of the interference beam.

In the former case, disturbance oscillation, like atmospheric swing, results in fluctuation of the phase term $\phi$ in the expression (1). This will cause noise in measuring the phase term p(t), thereby causing the accuracy of measurement to be reduced.

As the latter method (i.e., the reflectivity measuring method) aims at measurement of temperature changes and plasma density changes of a sample, it is impossible to obtain thermo-elastic characteristics such as thermal expansion ratio, etc. of a sample. And as only the information in thermal diffusion length can be obtained thereby, the method has such a defect that the depths of a sample can not be evaluated. Furthermore, the method is basically applicable only to samples of which reflectivity can change due to the temperature change.

SUMMARY OF THE INVENTION

It is therefore the first object of the invention to provide a sample evaluating method by thermal expansion displacement, by which the real thermal expansion displacement of a sample can be measured without being influenced by such disturbances as change in the reflectivity of a sample due to temperature change and plasma density change of a sample.

In order to accomplish the first object, the following first to third inventions are provided, and each of these three inventions can achieve the first object independently.

In order to accomplish the first object, the first invention is composed as a method for sample evaluating by measuring thermal expansion displacement on the surface of the sample, which is produced by irradiating thereto an excitation beam whose intensity is cyclically (frequency:F) modulated. Characterized in that a measuring beam (beam 1) having a vibration frequency $F_1$ is irradiated to the surface position of the sample which is subjected to thermal expansion by irradiation of the excitation beam. The reflection beam thereof is interfered with a reference beam (beam 2) having a vibration frequency $F_2$. Electric signals E to which the interference beam is photoelectrically converted are taken out, and thereafter beat wave signals $E_1$ (Beat frequency: $F_b$ ($F_b = F_1 - F_2$)) of electric signals E are obtained. The beat wave signals $E_1$ are binarized and converted to binary signals $E_2$, and components of the frequency $F - F_b$ or $F + F_b$ are extracted from the binary signal $E_2$, thereby causing the sample to be evaluated by the amplitude and phase of the component.

In order to accomplish the first object of the invention, the second invention is composed as a sample evaluating method by measuring thermal expansion displacement on the surface of the sample, which is produced by irradiating thereto an excitation beam of which intensity is cyclically (frequency: F) modulated. The method is characterized in that measuring beam (beam 1) having a vibration frequency $F_1$ is irradiated to the surface position of the sample which is subjected to thermal expansion by irradiation of the excitation beam. The reflection beam thereof is interfered with a reference beam (beam 2) having a vibration frequency $F_2$. Electric signals E to which the interference beam is photoelectrically converted are taken out, thereafter beat wave signals $E_1$ (Beat frequency: $F_b (F_b = F_1 - F_2)$) of electric signals E are obtained. The beat wave signals $E_1$ are binarized and converted to binary signals $E_2$, and delay signals $E_b$, which are delayed by time $\tau$ from the binary signals $E_2$ are created. A signal component $V_a$ regarding the frequency F is extracted from a multiplication signal $V_t$ obtained by multiplying the binary signals $E_2$ by the delay signals $E_b$, thereby causing the sample to be evaluated by the amplitude and phase of the signal component $V_a$.

In order to accomplish the first object of the invention, the third invention is composed as a sample evaluating method by measuring thermal expansion displacement on the surface of the sample, which is produced by irradiating thereto an excitation beam of which intensity is cyclically (frequency: F) modulated. The method is characterized in that a measuring beam (beam 1) having a vibration frequency $F_1$ is irradiated to the surface position of the sample which is subjected to thermal expansion by irradiation of the excitation beam. A reflection beam thereof is interfered with a reference beam (beam 2) having a vibration frequency $F_2$, and electric signals E to which the interference beam is photoelectrically converted are taken out. Thereafter beat wave signals $E_1$ (Beat frequency: $F_b (F_b = F_1 - F_2)$) of electric signals E are obtained, and the beat wave signals $E_1$ are binarized and converted to binary signals $E_2$. A component Vs of the frequency F of signals $V_u$ which the binary signals $E_2$ are multiplied by the local oscillating signal $E_b$ of frequency $F_b$ and a component $V_c$ of the frequency F of signals $V_n$ which the signals $E_4$ of which phase is different by 90° from the signal $E_2$ are multiplied by the local oscillating signal $E_b$ of frequency $F_b$ are extracted, and output $V_o$ having a variable concerning to only the phase change $P_{(t)}$ of the beam 1 on account of the thermal expansion displacement of a sample is operated by the components Vs and $V_c$, thereby causing the sample to be evaluated by the output $V_o$.

Furthermore, it is the second object of the invention to provide a sample evaluating method by using thermal expansion displacement, by which it is attempted that, by concurrently utilizing the excitation beam itself as measuring beam, time and labor are not needed in the optic axis alignment of both the beams, the optical system is simplified and the cost is decreased. Further the real thermal expansion displacement of a sample can be measured without being influenced by such a disturbance as change in the reflectivity of the sample due to temperature changes and plasma density changes of the sample.

In order to achieve the second object of the invention, the fourth invention is composed as a sample evaluating method by measuring thermal expansion displacement on the surface of the sample, which is produced by irradiating thereto an excitation beam of which intensity is cyclically (frequency: F) modulated. The method is characterized in that a measuring beam (beam 1) having a vibration frequency $F_1$ is irradiated to the surface position of the sample which is subjected to thermal expansion by irradiation of the excitation beam. A reflection beam thereof is interfered with a reference beam (beam 2) having a vibration frequency $F_2$, and electric signals E to which the interference beam is photoelectrically converted are taken out. Thereafter beat wave signals $E_1$ (Beat frequency: $F_b (F_b = F_1 - F_2)$) of electric signals E are obtained, and the beat wave signals $E_1$ are binarized and converted to binary signals $E_2$. A component of the frequency $F - F_b$ or $F + F_b$ is extracted from the binary signals $E_2$, thereby causing the sample to be evaluated by the amplitude and phase of the component.

Therefore, the fourth invention relates to what the excitation beam in the first invention is concurrently used as measuring beam. So, the reference number thereof is common.

In order to achieve the second object of the invention, the fifth invention is composed as a method for sample evaluating by measuring thermal expansion displacement on the surface of the sample, which is produced by irradiating thereto an excitation beam of which intensity is cyclically (frequency: F) modulated. The method is characterized in that measuring beam (beam 1) having a vibration frequency $F_1$ of which intensity is modulated with the frequency F is irradiated, and the reflection beam thereof is interfered with a reference beam (beam 2) having a vibration frequency $F_2$. Electric signals E to which the interference beam is photoelectrically converted are taken out, and thereafter beat wave signals $E_1$ (Beat frequency: $F_b (F_b = F_1 - F_2)$) of electric signals E are obtained. The beat wave signals $E_1$ are binarized and converted to binary signals $E_2$. Delay signals $E_b$, which are delayed by time $\tau$ from the binary signals $E_2$, are created, and signal component $V_a$ regarding the frequency F is extracted from a multiplication signal $V_t$ obtained by multiplying the binary signals $E_2$ by the delay signals $E_b$, thereby causing the sample to be evaluated by the amplitude and phase of the signal component $V_a$.

In order to accomplish the second object of the invention, the sixth invention is composed as a method for sample evaluating by measuring thermal expansion displacement on the surface of the sample, which is produced by irradiating thereto an excitation beam of which intensity is cyclically (frequency: F) modulated. The method characterized in that measuring beam (beam 1) having a vibration frequency $F_1$ of which intensity is modulated with the frequency F is irradiated, and the reflection beam thereof is interfered with a reference beam (beam 2) having a vibration frequency $F_2$. Electric signals E to which the interference beam is photoelectrically converted are taken out, and thereafter beat wave signals $E_1$ (Beat frequency: $F_b (F_b = F_1 - F_2)$) of electric signals E are obtained. The beat wave signals $E_1$ are binarized and converted to binary signals $E_2$. A component Vs of the frequency F of signals $V_u$ which the binary signals $E_2$ are multiplied by the local oscillating signals $E_b$ of frequency $F_b$ and a component $V_c$ of the frequency F of signals $V_n$ which the signals $E_4$ of which phase is different by 90° from the signals $E_2$ are multiplied by the local oscillating signals $E_b$ of frequency $F_b$ are extracted, and output $V_o$ having a variable concerning to only the phase change $P_{(t)}$ of the beam 1 on account of the thermal expansion displacement of a sample is operated by the components $V_s$ and $V_c$, thereby causing the sample to be evaluated by the output $V_o$.

In each of the invention embodiments above discussed, the step of binarizing the beat wave signals, i.e., converting the beat wave signals to binary signals, enables measurement of thermal expansion displacement uninfluenced by changes in reflectivity of the sample due to temperature change and plasma density change of the sample.

DETAILED DESCRIPTION OF THE PREFERRED EMBODIMENTS

Figure 1:
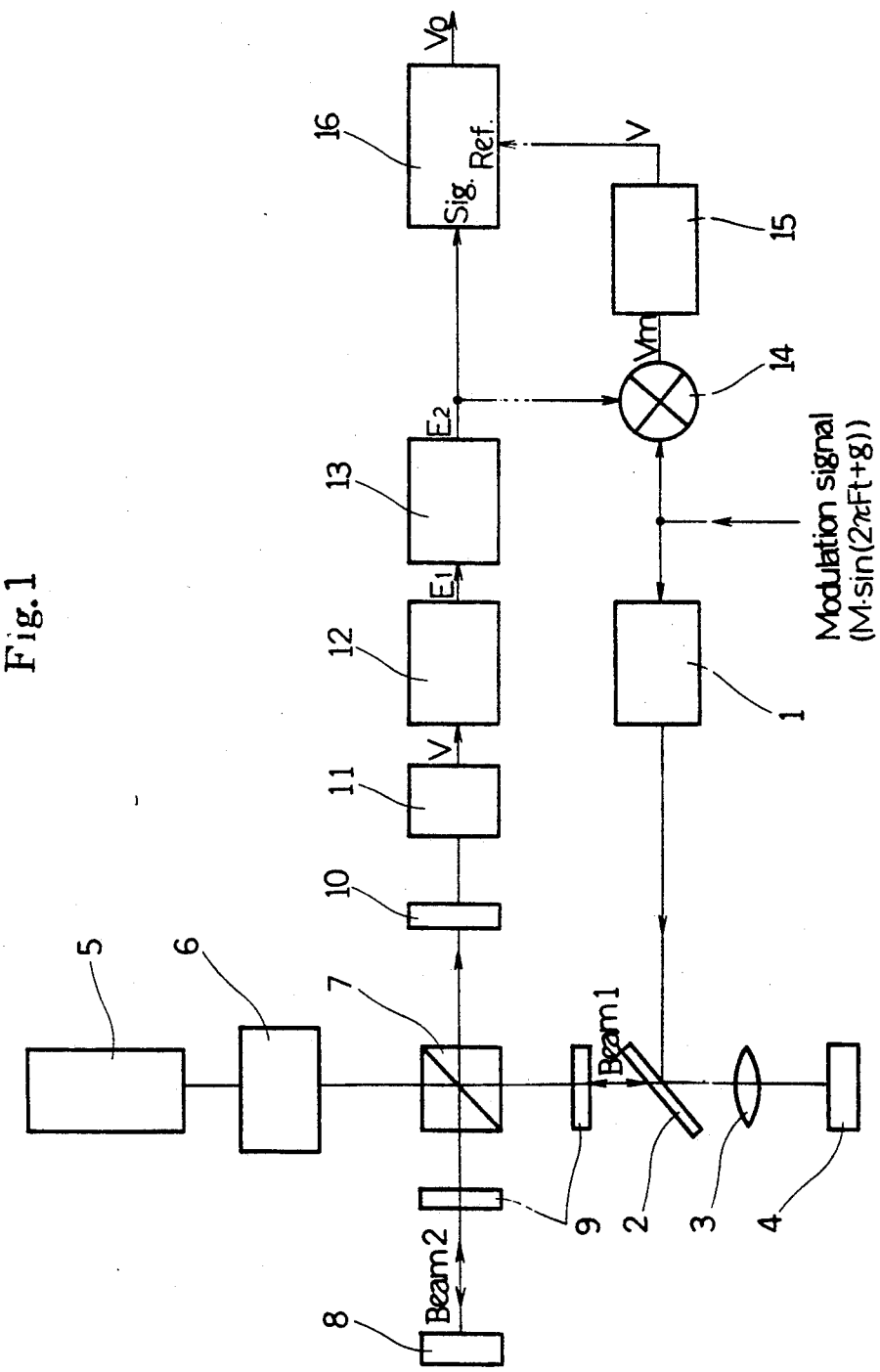
FIG. 1 is a block diagram showing a device of a first embodiment of the invention.

With reference to FIG. 1, the first embodiment of the invention is described.

As shown in FIG. 1, a semi-conductor laser 1 is utilized as an excitation laser by which thermal expansion displacement is produced in the sample 4. The intensity of the excitation beam is modulated with the frequency F by changes of injection current to the laser 1. The excitation beam is reflected by a dichroic mirror 2, condensed by a lens 3 and is irradiated to the sample 4.

The sample 4 is cyclically heated by this cyclic irradiation of beam, thereby causing thermal expansion displacement to occur. The thermal expansion displacement is measured by a laser beam interference method which is described below.

A He-Ne laser 5 is used as measuring laser. Measuring beam *Beam 1) and reference beam (Beam 2) whose optical frequency difference becomes $F_b$ and whose polarization plane is orthogonal are generated by a frequency shifter 6. These beams are divided into two with a polarized beam splitter 7, the beam 1 of which is transmitted through the dichroic mirror 2, is condensed with the lens 3 and irradiated to the sample 4, and the beam 2 of which is irradiated to a mirror 8. As the polarization plane thereof is changed by 90° after the reflection beam of the beam 1 which comes from the sample passes through a ¼ wave plate 9, it is reflected by the polarized beam splitter 7 this time. As well, the reflection beam of the beam 2 which comes from the mirror 8 is transmitted through the polarized beam splitter 7. These laser beams are interfered with each other by transmitting them through a polarizing plate 10 since the beams are intersected at a right angle with each other, and the interfered beams are detected by a photoelectric converter 11.

The beat wave signal $E_1$ in the interference beam is taken out by passing the output V from the photoelectric converter 11 through a filter 12. The beat wave signal $E_1$ is given as shown below:

$$E_1 = A \cos(2\pi F_b t + P(t) + \phi) \quad (2)$$

Where A is a value which depends upon a sample and the interference optical system, etc. (corresponding to $C_2$ in the expression (1)), P(t) is a phase change of the beam 1 by thermal expansion displacement of the sample, and $\phi$ is a phase difference by the difference of optical path length between the beams 1 and 2 when the P(t) is zero (i.e., there is no thermal expansion displacement). Assuming that the amplitude of vibrations of the sample is L and the phase is P, P(t) is given as described below.

$$P(t) = (4\pi/\lambda) \cdot L \sin(2\pi F t + P) \quad (3)$$

Here, in case of $L << \lambda$, the component V which has the frequency $F_b - F$ of a signal $E_1$ is:

$$V = (2\pi/\lambda) \cdot AL \cos(2\pi (F_b - F)t - P + \phi) \quad (4)$$

It is possible to measure the thermal expansion displacement of a sample by measuring the amplitude L and phase P of a signal of this frequency component. However, as described above, in the case that A fluctuates as it is influenced by the reflectivity of a sample, which changes with the temperature change and plasma density change of the sample, noise occurs and accurate thermal expansion displacement can not be measured.

So, in the embodiment, the value of $E_1$ is compared with the zero level (threshold value). Waveform conversion is executed by binarization with the comparator 13 so that $E_1$ can be equal to V (i.e., $E_1 = V$) in case that the $E_1$ is more than the zero level, and $E_1$ can be equal to $-V$ (i.e., $E_1 = -V$) in case that the $E_1$ is less than the zero level. After this waveform conversion, the signal $E_2$ is expressed as follows;

$$E_2 = \frac{4V}{\pi} \cos(2\pi F_b t + P(t) + \phi) + \quad (5)$$

(High-frequency component)

In this case, the signal component having the frequency of $F_b - F$ when $L << \pi$ in $E_2$ is;

$$V = \frac{4V}{\lambda} L \cos(2\pi (F_b - F)t - P + \phi) \quad (6)$$

As A is not included in the V, the thermal expansion vibrations (amplitude L and Phase P) can be measured accurately.

In order to extract the signal component having the frequency of $F_b - F$ from the $E_2$, it can be considered that a frequency analyzer or an FM tuner is utilized. However, when the signal level is low, it is proper that a synchronous detection system is utilized. In this case, synchronous detection may be executed with signals having the frequency $F_b - F$ as reference signals. But as an optical interferometer is generally liable to be influenced by atmospheric swing, disturbance vibrations, etc., they will become noises, thereby causing timelike fluctuation to be brought in the phase $\phi$ in the expressions (2) and (5). The fluctuation of $\phi$ results in fluctuation of V, and the thermal expansion displacement can not be measured stably.

Hence, in the embodiment, $E_2$ is first multiplied by a fluctuation signal ($M \cdot \sin(2\pi F_t + q)$) with a multiplicator 14. M and q are the constants that have been already known. After the multiplication, the signal $V_m$ is:

$$V_m = R \cos(2\pi(F_b+F)t+\phi+q) + R \cos(2\pi(F_b-F)t+\phi-q) \tag{7}$$

$(R = 2MV/\pi)$

Then, the signal $V_r$ of the second term in the right side of the above expression is taken out by passing the $V_m$ through a filter 15. Subsequently, synchronous detection is executed with this $V_r$ utilized as reference signal. In the case that the synchronous detection 16 is executed as the Vr utilized as reference signal as the $V_r$ includes the phase $\phi$, the influence of the phase $\phi$ at V is counterbalanced. The synchronous detection output $V_o$ is:

$$V_o = \frac{4V}{\lambda} L\cos(P + q) \tag{8}$$

Therefore, the phase $\phi$ can be eliminated, and $V_o$ can be stably measured, thereby causing the thermal expansion displacement (L, P) to be accurately measured.

Furthermore, the above description deals with extraction of the frequency $F_b - F$. However, at the $E_2$, the component of the frequency $F_b + F$ also includes information of thermal expansion displacement. Therefore, the thermal expansion displacement can be measured by using the signal of the first term in the right side of $V_m$ of the expression (7).

Figure 2:
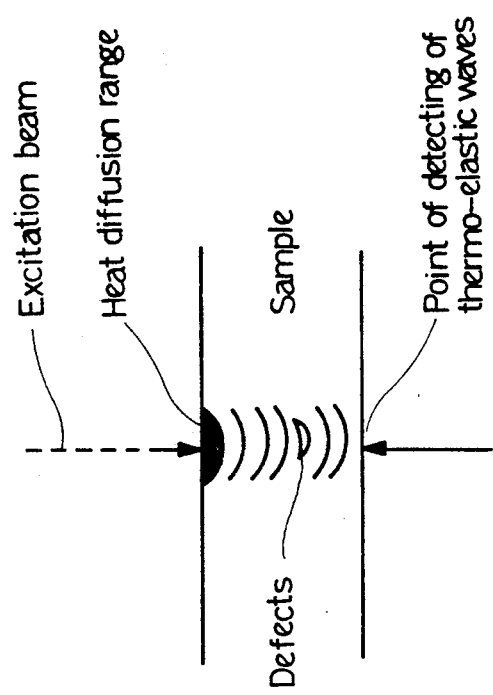
FIG. 2 is a general view showing a method for detecting a defect in a sample.

FIG. 2 shows a detection method of internal defects of a sample. Namely, FIG. 2 shows such a composition that distorted waves due to thermal expansion displacement can be detected at the rear side of the sample or at a point far from the point of irradiation by irradiating a laser beam by which thermal expansion signals can be induced on the surface of the sample. In this case, the detected displacement includes information (elasticity characteristics) in propagation of elastic waves, thereby causing internal defects and surface cracks of the sample to be detected. In the above conventional reflectivity measurement method, as only the information in the diffusion length of the excitation beam can be obtained, such an evaluation can not be executed.

The detection method of internal defects, which is shown in FIG. 2, is applicable to the second through, the sixth embodiments described below as well.

Figure 3:
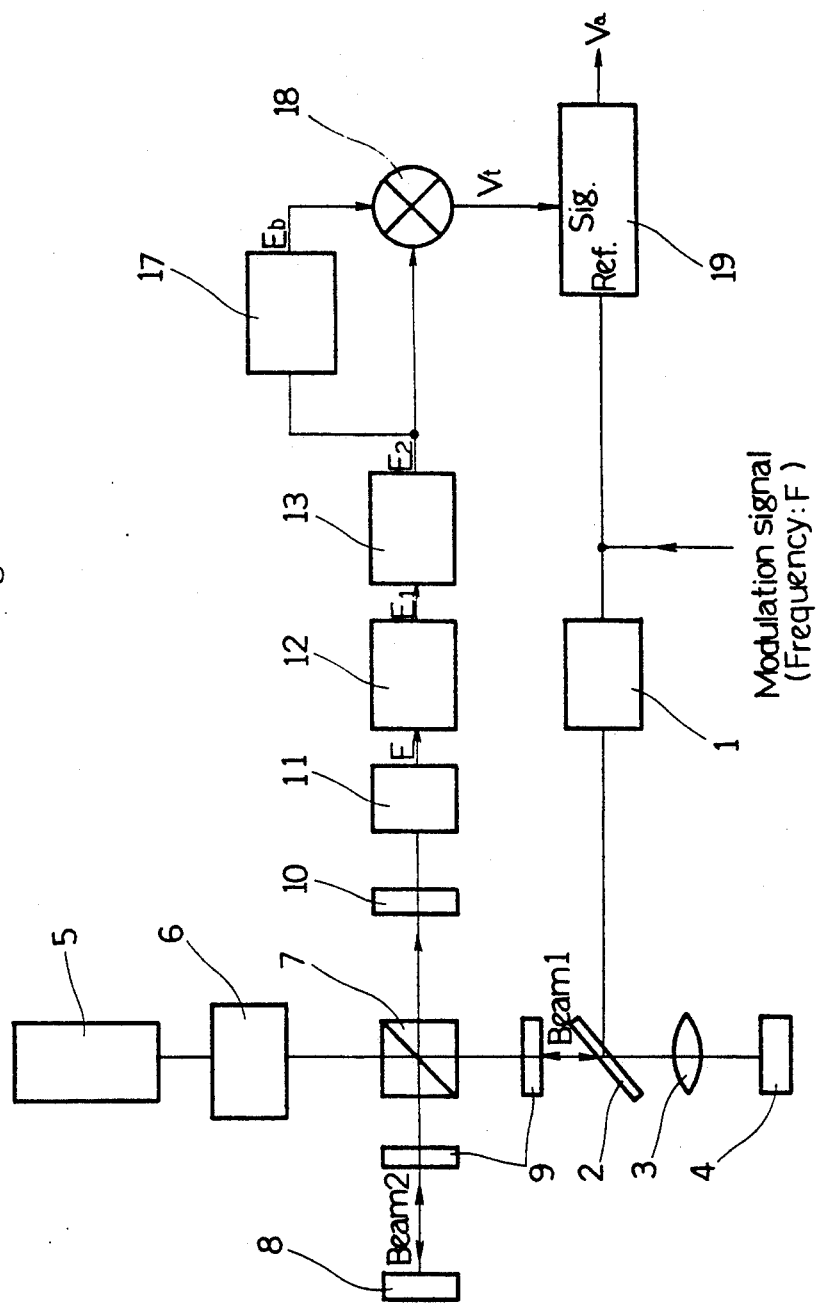
FIG. 3 is a block diagram showing a device of a second embodiment of the invention.

With reference to FIG. 3, the ensuing description describes the second embodiment. In the embodiment, the details up to the point where the binary signals $E_2$ are produced (expression (5)) by means of the comparator 13 are the same as those in the first embodiment.

In the embodiment, the binary signals $E_2$ are inputted in the delay circuit 17, thereby causing the delay signals $E_b$, which are delayed by time $\tau$ from the above binary signals $E_2$, to be generated. The delay signals $E_b$ are given with the following expression (9).

$$E_b = \frac{4V}{\pi} \cos(2\pi F b(t - \tau) + P(t - \tau) + \phi(t - \tau)) + \tag{9}$$

(Harmonic content)

The delay operation in the above delay circuit 17 is triggered at the time when the binary signal $E_2$ becomes zero. Namely, the above delay circuit 17 can be realized by utilizing a pulse generation circuit by a gate circuit or a delay line, etc.

Moreover, the delay time $\tau$ is set on the basis of the frequency F of the modulation signal, the beat frequency $F_b$ and the sample characteristics.

And a multiplication signal $V_t$ can be obtained by multiplying the binary signals $E_2$ and the delay signals $E_b$ by means of the multiplicator 18. This multiplication signal $V_t$ can be expressed with the following expression (10).

$$V_t = \tag{10}$$

$R\cos(2\pi Fb(2t - \tau) + P(t) + P(t - \tau) + \phi(t) + \phi(t - \tau)) +$ $R\cos(2\pi Fb\tau + P(t) - P(t - \tau) + \phi(t) - \phi(t - \tau)),$ where $R = 2V/\pi$.

Moreover, the description of harmonic content which appears in the expression (9) is omitted in the expression (10). This is because the description for extracting the signal components regarding the frequency F described later is facilitated. Actually, the harmonic component can be eliminated, for instance, by processing with a filter.

And the phase difference $\phi(t)$ is fluctuated with a comparatively low frequency as shown in the above, and the cycle of fluctuation is comparatively long. Therefore, when the delay time $\tau$ which is set by the delay circuit 17 is sufficiently smaller than the cycle of the fluctuation (for instance, when $\tau$ is less than several milliseconds), it can be assumed that the phase difference $\phi(t)$ at the time t remarkably approximates to the phase difference $\phi(t-\tau)$ at the time $(t-\tau)$, and the following expression (11) can be established.

$$\phi(t) - \phi(t-\tau) \approx 0 \tag{11}$$

Hence, the multiplication signal $V_t$ of the above expression (10) is expressed with the following expression;

$$V_t = R \cos(2\pi F_b(2t-\tau) + P(t) + P(t-\tau) + 2\phi(t)) + R \cos(2\pi F_b\tau + Q(t)) \tag{12}$$

At the expression (12), $$Q(t) = P(t) - P(t - \tau) \tag{13}$$
$$= S\cos(2\pi F_t - \pi F\tau + q)$$

And $$S = \frac{8\pi}{\lambda} L\sin(\pi F\tau) \tag{14}$$

That is, the multiplication of the binary signals $E_2$ by the delay signals $E_b$ can produce the signal components in which the phase difference $\phi(t)$, $\phi(t-\tau)$ can be counterbalanced.

Next, the signal components Va having the frequency F are extracted from the multiplication signal $V_t$ of the expression (12). The operation for extracting the signal component $V_a$ is executed by using a synchronous detector 19 which is considered to be preferable in dealing with signals of which level is low, and the modulation signals having the frequency F are applied as reference signals to the synchronous detector 19. Also, it is possible to utilize a frequency analyzer, a band-pass filter, etc. instead of the synchronous detector 19.

Here, the first term in the right side of the expression (12) means the signal component regarding the main frequency ($2F_b$), and the second term thereof means the signal component regarding the main frequency (F). Namely, as the frequency system of the signal component of the first term thereof is different from that of the second term thereof, respectively, it is possible to extract either of the signal components from the multiplication signal $V_t$.

Hence, when $L \ll \lambda$, the second term in the right side thereof is developed as shown below;

The second term in the right side of the expression $$(12) = R\cos(2\pi F_b \tau + Q(t)) = \quad (15)$$
$$R\cos(2\pi F_b \tau + S\cos(2\pi F_t - \pi F \tau + q)) =$$
$$R\cos(2\pi F_b \tau)\cos(S\cos(2\pi F_t - \pi F \tau + q)) -$$
$$R\sin(2\pi F_b \tau)\sin(S\cos(2\pi F_t - \pi F \tau + q)) \approx$$
$$R\cos(2\pi F_b \tau) \cdot \{1 - 2J_2(S)\cos(2(2\pi F_t - \pi F \tau + q))\} +$$
$$R\sin(2\pi F_b \tau) \cdot (S\cos(2\pi F_t - \pi F \tau + q))$$

where $J_2$ (S) is the secondary Bessel function.

And the signal component $V_a$ having the frequency F in the expression (15) is the second term in the right side thereof, and the second term in the right side thereof can be extracted by the synchronous detector 19. Namely, the signal component $V_a$ is expressed as the following expression;

$$V_a = R \sin (2\pi F_b \tau) \cdot (S \cos (2\pi F_t - \pi F \tau + q)) \quad (16)$$

According to the expression (16), as the signal component Va does not include the coefficient A and the phase difference $\phi(t)$, it does not depend upon the kind of a sample and the interference optical system, etc. and is not subjected to influence of such noises as atmospheric swing and disturbance vibrations, etc.

Therefore, according to the embodiment, it is possible to stably measure the signal component $V_a$, thereby causing the thermal expansion vibrations (amplitude and phase) to be accurately measured.

Furthermore, in the embodiment, as the amplitude and phase of the signal component Va change to the delay time $\tau$ as specified in the expression (16), attention must be paid to setting the delay time $\tau$. And in case that a synchronous detector or other filter circuit not having any phase measuring feature is used, it is possible to obtain the amplitude L of the thermal expansion displacement and the phase q from the amplitude value of the signal component Va by more than two kinds of the delay time $\tau$.

Also, in the embodiment, the signal component pertaining to the frequency F of the second term in the right side of the expression (15) is extracted as signal component $V_a$ pertaining to the frequency F extracted by the multiplication signal $V_t$ from the multiplicator 18. However, the extraction is not limited to the above example, the signal component pertaining to the frequency 2F of the first term in the right side thereof can be extracted, too. However, in this case, means for synchronizing this frequency with the frequency of modulation signals which are used as reference must be separately provided in the synchronous detector 19.

As shown in the above, an optical interferometer is generally liable to be influenced by atmospheric swing and disturbance vibrations, etc. and they can be turned into noises, thereby causing timelike fluctuation to be brought to the phase $\phi(t)$ in the expressions (2) and (4). Therefore, as $\phi(t)$ changes, it is impossible to stably measure the thermal expansion displacement of a sample.

Figure 4:
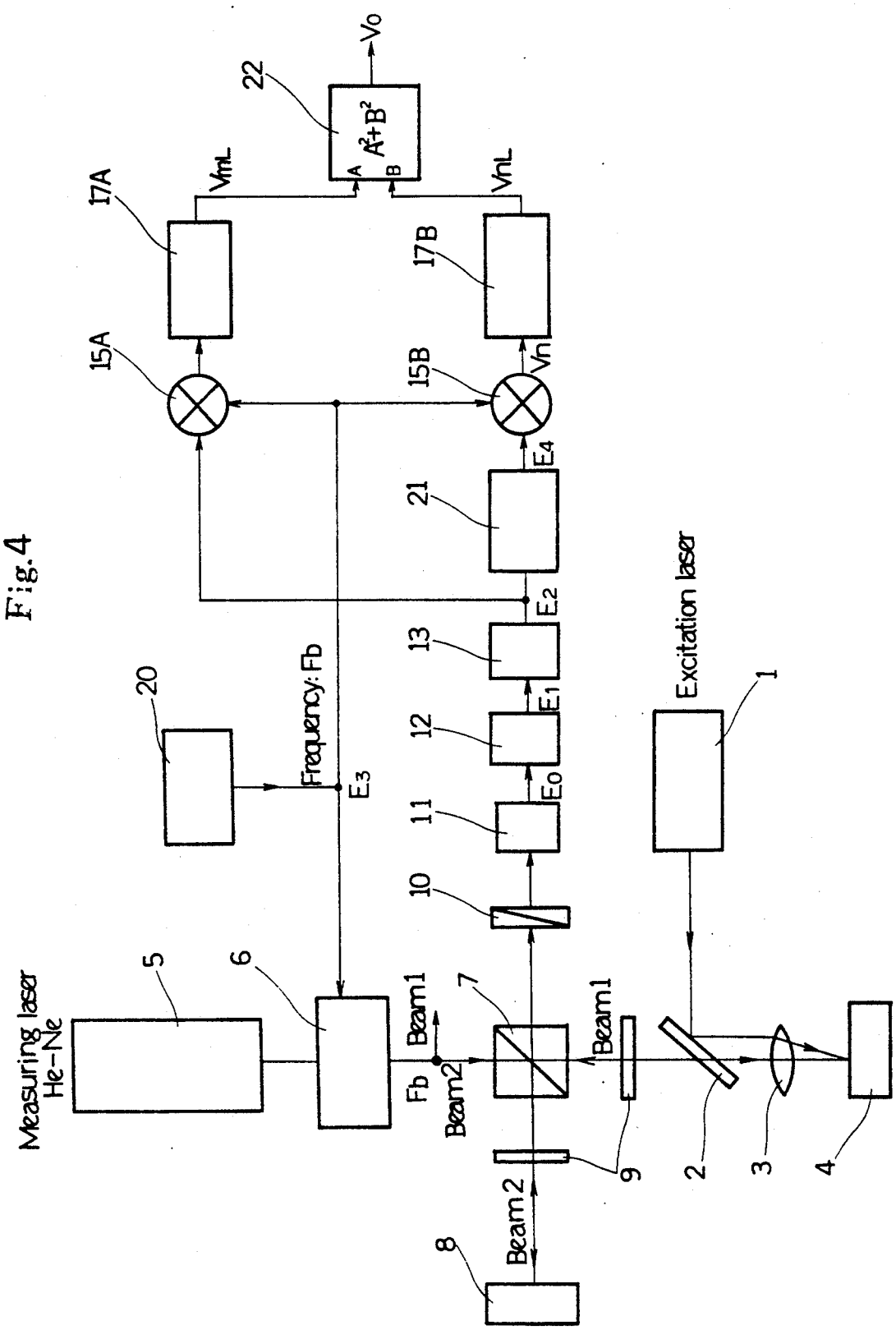
FIG. 4 is a block diagram showing a device of a third embodiment of the invention.

The third embodiment for eliminating the above $\phi(t)$ is described with reference to FIG. 4. The method utilized up to securing the binary signals $E_2$ is the same as that in the first and second embodiments. The above signal $E_2$ is multiplied by the local oscillating signals $E_b$ of the frequency $F_b$ from the oscillator 20 by means of a multiplicator $15_A$.

$$E_b = K \cos (2\pi F_b t) \quad (17)$$

where K is a constant. The signal $V_m$ after the multiplication is expressed with the following expression (18):

$$V_u = R \cos (P(t) + \phi(t)) + R \cos (4\pi F_b t + P(t) + \phi(t)) \quad (18)$$

$$(R = 2VK/\pi)$$

It is considered that the high-frequency content can be eliminated in the subsequent filtering processing, and the description of the high-frequency content is omitted in the expression (18).

Next, signals $V_{mL}$ in which high-frequency content (Frequency 2Fb band) are eliminated are generated by the filter $17_A$. When P(t) is small (the vibration amplitude is sufficiently small in comparison with the wave length $\lambda$), the $V_{mL}$ is expressed with the following expression (19);

$$VmL \approx R \cos (\phi(t)) - RP(t) \sin (\phi(t)) \quad (19)$$

Next, the signal $E_4$ of which phase is different by 90° from the binary signal $E_2$ is created by a phase-shift circuit 21;

$$E_4 = (4V/\pi) \cos (2\pi F_b t + P(t) + \phi(t) - \pi/2) + \text{(High-frequency content)} \quad (20)$$

After $V_n$ is obtained by multiplying the above $E_4$ by the local oscillating signal $E_b$ of the frequency $F_b$ by means of a multiplicator $15_B$ as well as in the processing by the above expression (18), the signal $V_{nL}$ of which high frequency content (frequency $2F_b$ band) is eliminated is created by a filter $17_b$. When the P (t) is small, the $V_{nL}$ is expressed with the following expression (21).

$$V_{nL} \approx R \sin (\phi(t)) + RP(t) \cos (\phi(t)) \quad (21)$$

$\phi(t)$ is fluctuated to the elapse of time by disturbance vibrations, etc. However, generally, the frequency of this fluctuation is a low frequency (less than scores of Hz). Therefore, when the frequency of changes of P (t) is large in comparison with the frequency of $\phi(t)$, only the second term of the expressions (19) and (21) can be taken out by filters $17_A$ and $17_B$. These outputs $V_s$ and $V_c$ are expressed with the following expressions;

$$V_s = -RP(t) \sin(\phi(t))$$

$$V_c = RP(t) \cos(\phi(t)) \qquad (22)$$

$\phi(t)$ is included in the expression (22). However, only the phase term P(t) can be extracted, thereby causing the thermal expansion displacement characteristics of a sample to be analyzed. In the embodiment, the root-sum of $V_s$ and $V_c$ is obtained by an operational circuit 22. The output $V_b$ thereof is;

$$V_b = (BP(t))^2 \qquad (23)$$

And the $\phi(t)$ is not included therein. Also, as $V_b$ is created by the binary signal $E_2$ (or signal $E_4$ of which phase is different by 90° from the $E_2$) and the local oscillating signal $E_b$, it is not influenced by such noises as disturbance vibrations, etc., thereby causing the vibrations to be stably detected.

Furthermore, as $V_b$ does not include a coefficient A in the expression (2), the thermal expansion displacement of a sample can be measured with high accuracy without being influenced by noises due to the reflectivity fluctuation suggested in the above point of problem.

Next, With reference to FIG. 5, the fourth embodiment is described below, in which the optic axes alignment of the excitation beam and the measuring beam is not needed as the excitation beam itself can be concurrently utilized as measuring beam.

Figure 6:
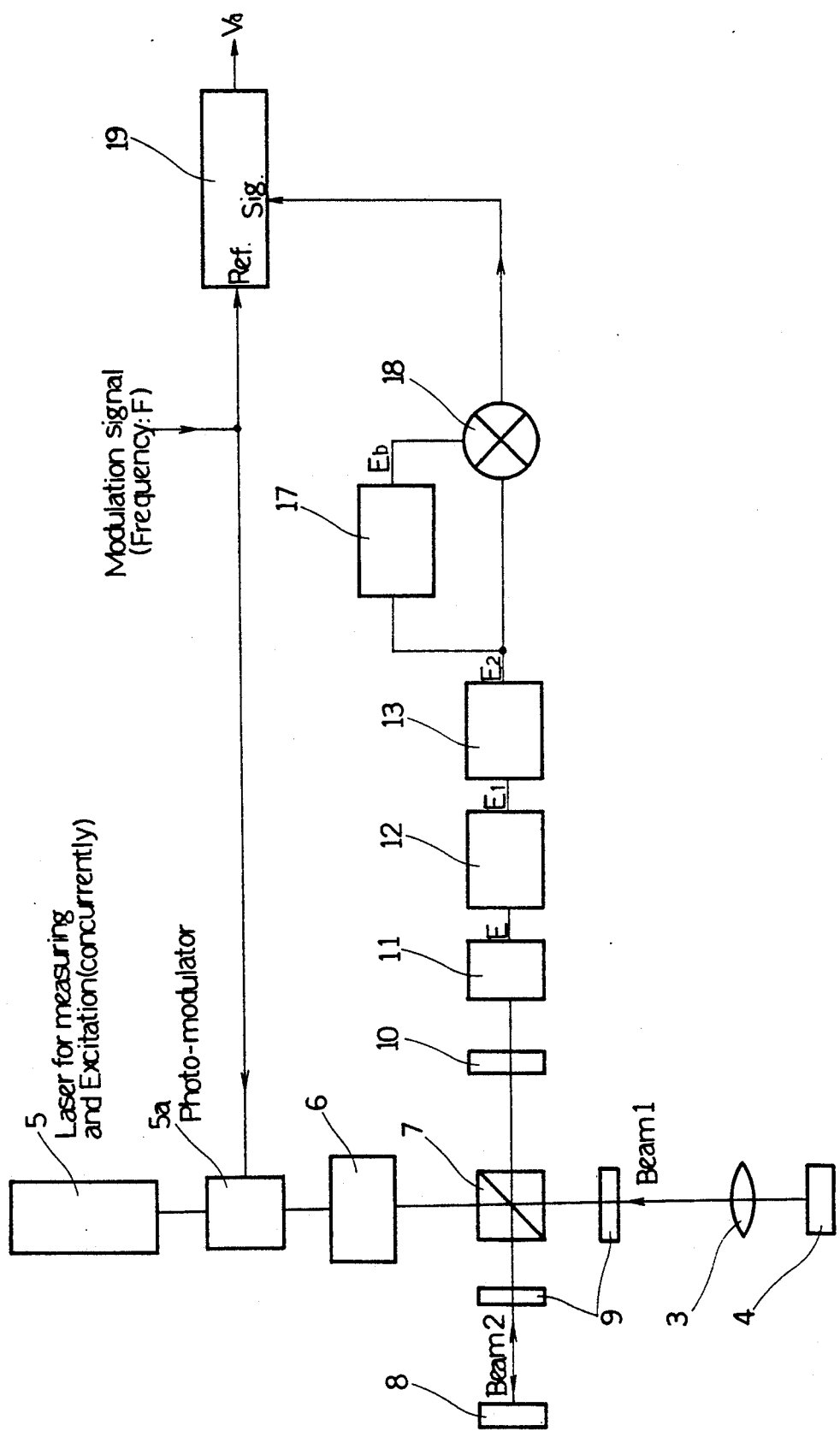
FIG. 6 is a block diagram showing a device of a fifth embodiment of the invention.
Figure 7:
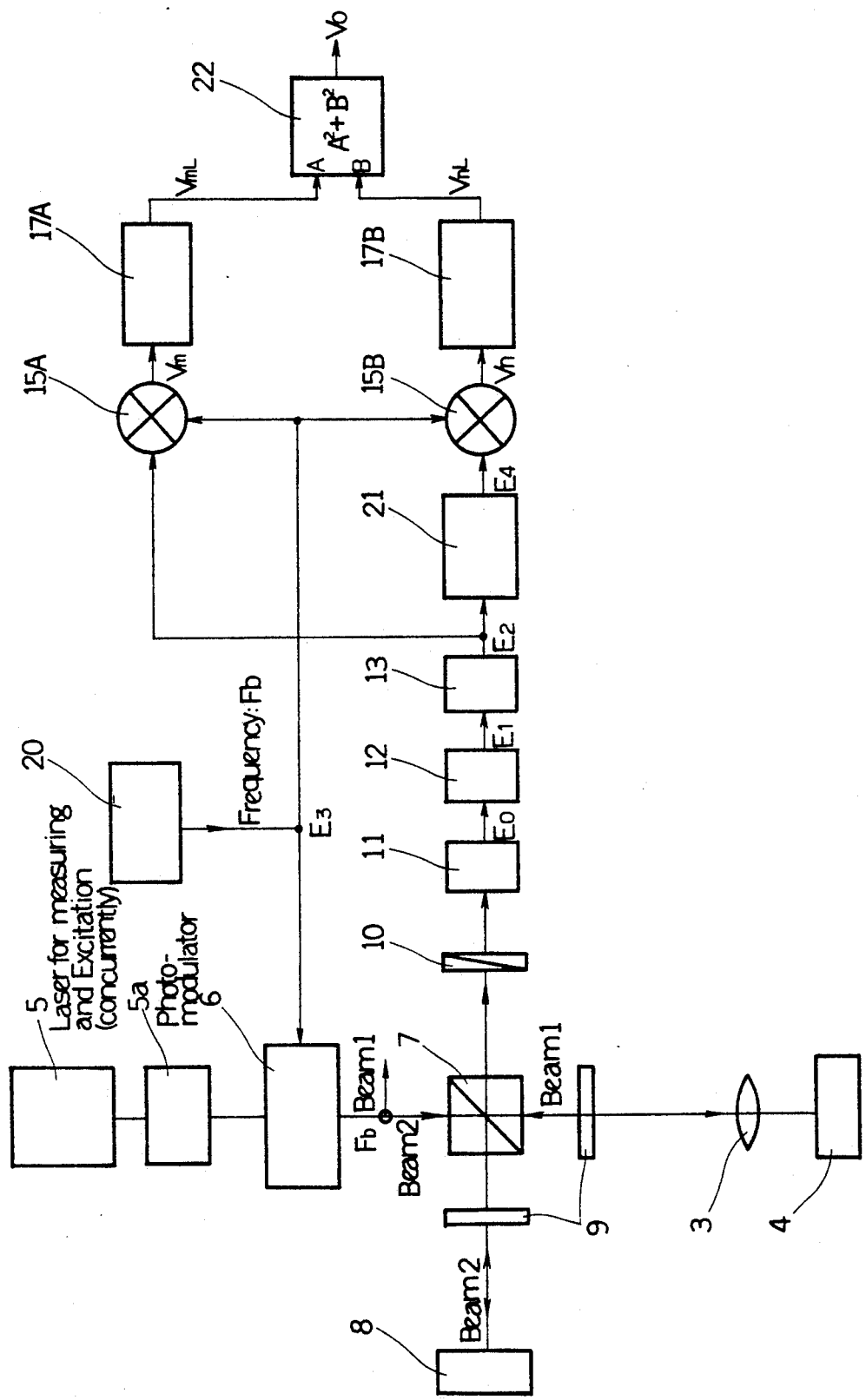
FIG. 7 is a block diagram showing a device of a sixth embodiment of the invention.
Figure 8:
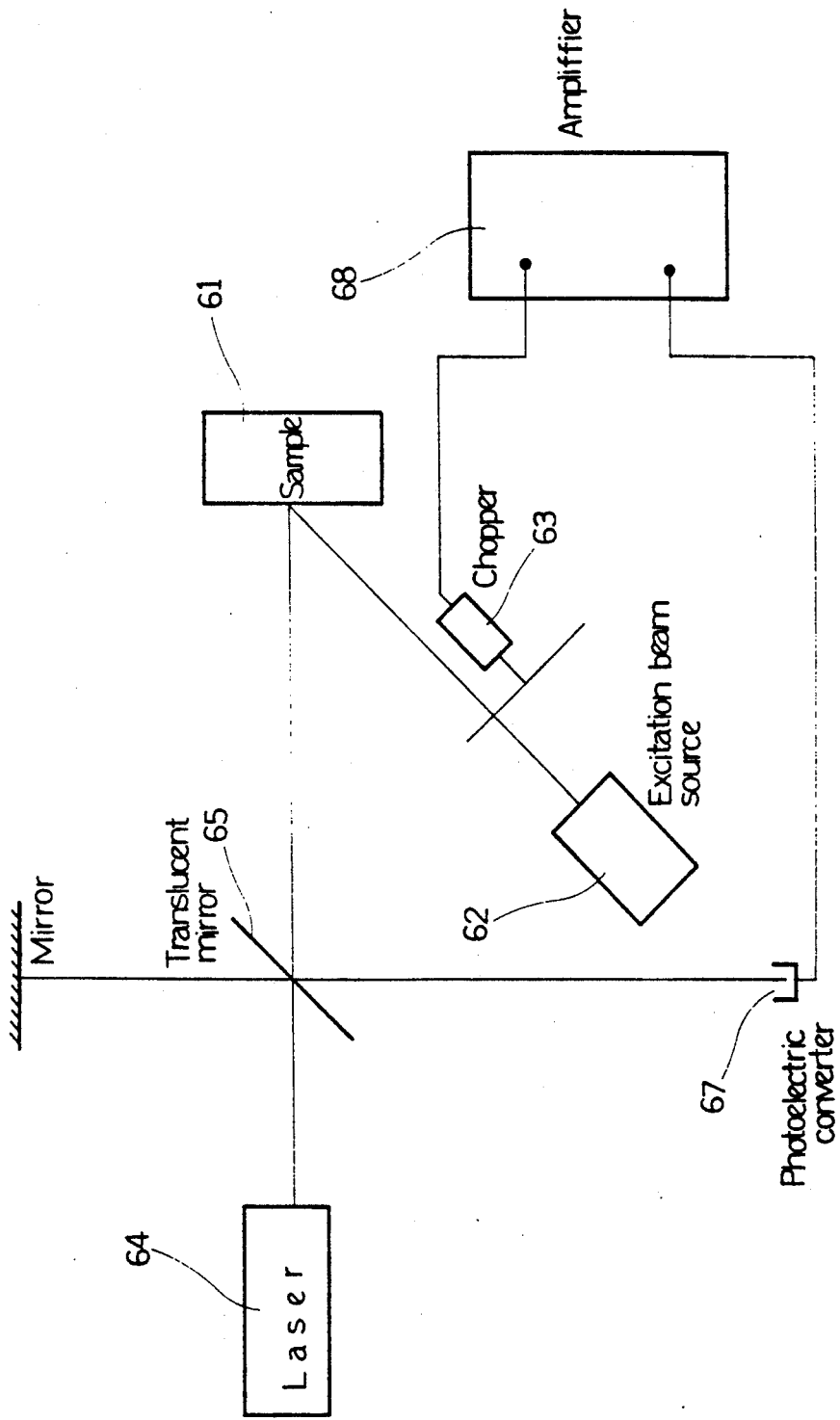
FIG. 8 is a general view showing a conventional sample evaluating method by using thermal expansion displacement.
Figure 9:
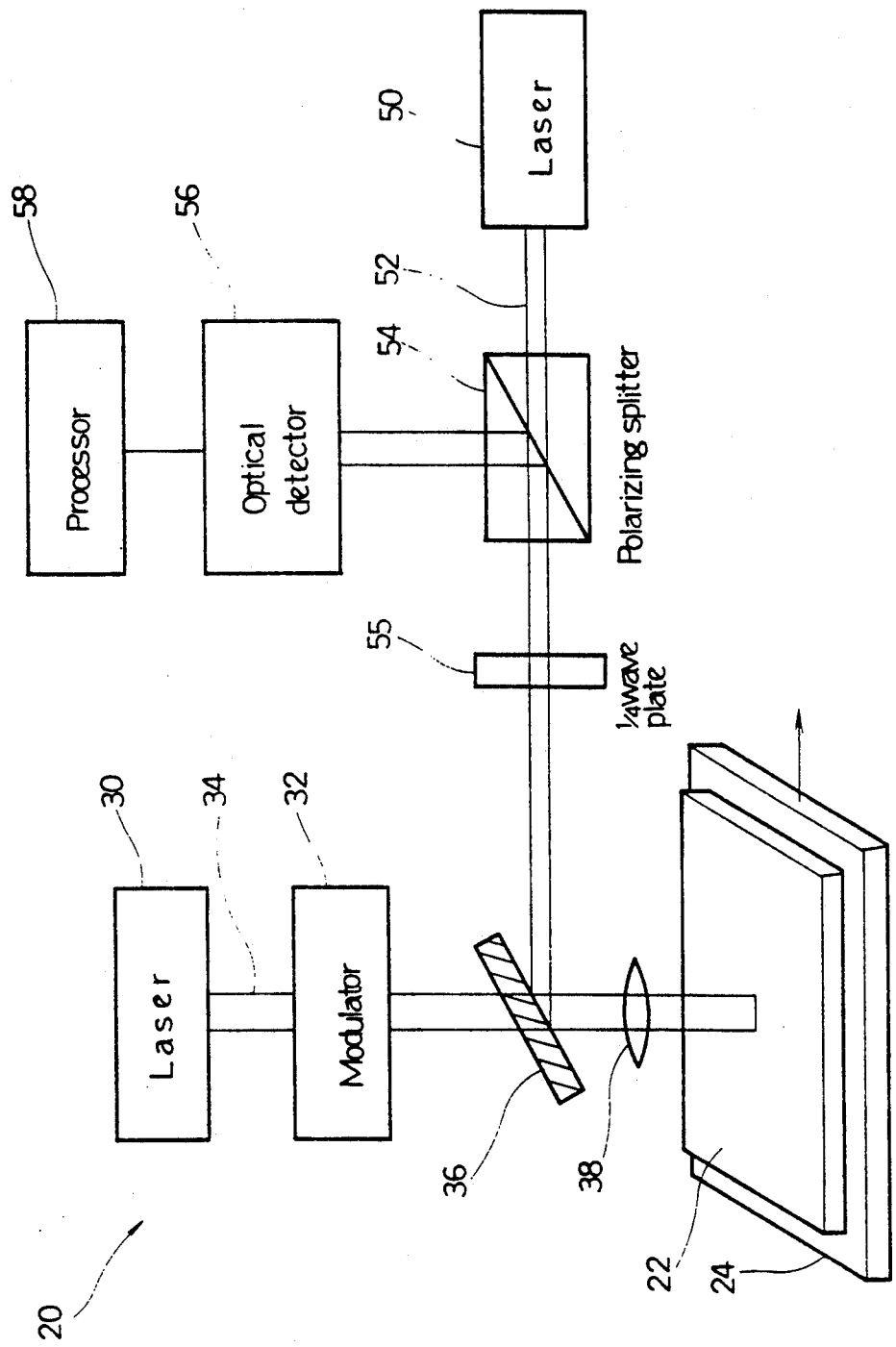
FIG. 9 is a general view showing a conventional sample evaluating method according to the reflectivity measuring method.

This embodiment is a modification of the first embodiment. However, the basic concept thereof (i.e., concurrently utilizing the excitation beam itself as measuring beam) can be applied to the second and the third embodiments as well. As the manner of application thereof is the same as that of this embodiment, FIG. 6 and FIG. 7 are attached only for showing the outline of the device, and the detailed description thereof is omitted herein. All the factors which are common in respective embodiments are given the same reference numbers, and furthermore, the reference numbers of the expressions are given the same number as well.

Figure 5:
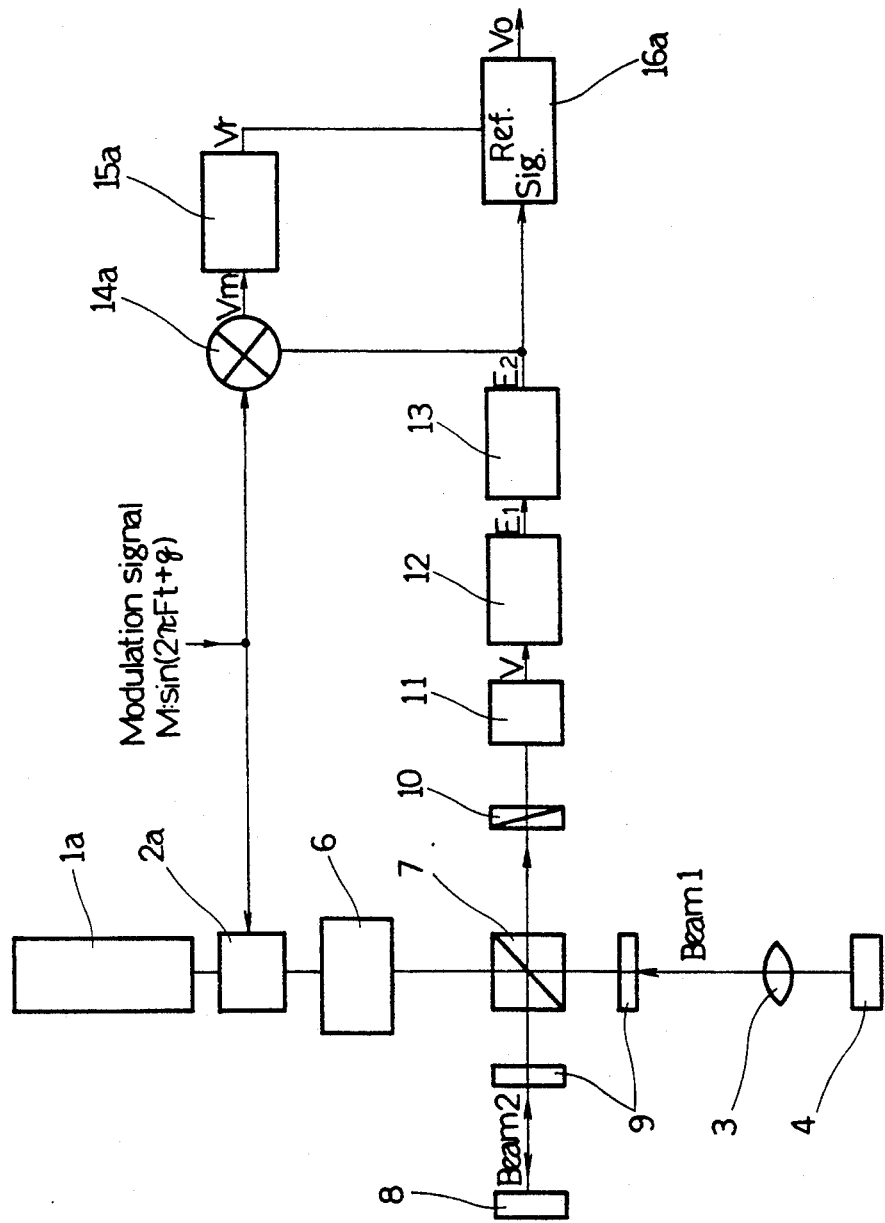
FIG. 5 is a block diagram showing a device of a fourth embodiment of the invention.

As shown in FIG. 5, thermal expansion displacement is given to a sample 4, and an argon ion laser 1a is used as laser to measure the thermal expansion displacement. Then, the intensity of the outgoing beam thereof is modulated with the frequency F by an optical modulator 2a, thereby causing beams 1 and 2, of which frequency difference is $F_b$ and of which polarization plane is orthogonal, to be created by a frequency shifter 6. These beams are divided into two by a polarized beam splitter 7, beam 1 (excitation beam) of which is condensed by a lens 3 and irradiated to the sample 4, and beam 2 (reference beam) of which is irradiated to the mirror 8.

As the polarization plane changes by 90° after the reflection beam of the beam 1 from the sample 4 passes through the ¼ wave plate 9, the reflection beam thereof is reflected by the polarized beam splitter 7 this time. As well, the reflection beam of the beam 2 from the mirror 8 can go through the polarized beam splitter 7. As these laser beams are intersected at a right angle, they are interfered by penetrating the polarizing plate 10, and the interfered beam can be received by the photoelectric converter 11.

The beat wave signal $E_1$ at the interfered beam is taken out by passing the output V from the photoelectric converter 11 through the filter 12. Using U (t) as modulation signal, the $E_1$ is given as follows;

$$E_1 = AU(t) \cos(2\pi F_b t + P(t) + \phi) \qquad (2)$$

(U (t) = 1 + m sin ($2\pi F_t$) m: Modulation ratio) where A is a value which depends upon the sample and the interference optical system, etc., P (t) is a phase change of the beam 1 by the expansion displacement of the sample, and $\phi$ is a phase difference by the difference of optical path length between the beam 1 and the beam 2 when the P (t) is zero.

When it is assumed that the amplitude of vibrations of the sample is L and the phase thereof is P, the P (t) is given as follows;

$$P(t) = \frac{4\pi}{\lambda} L \sin(2\pi F t + P) \qquad (3)$$

Herein, when $L << \lambda$, the signal component having the frequency $F_b - F$ of the $E_1$ is as follows;

$$V = \frac{2\pi}{\lambda} A L \cos(2\pi (F_b - F)t - P + \phi) \qquad (4)$$

It is possible to measure the thermal expansion displacement of the sample by measuring the amplitude and phase of a signal of this frequency content. However, in case that A is fluctuated by fluctuation of the reflectivity of the sample in accompanying with temperature changes, etc. of the sample as shown in the above, this becomes a noise, thereby causing the thermal expansion displacement not to be accurately measured. So, in the embodiment, the wave form conversion is executed through binarization by a comparator 12 so that in comparing the value of $E_1$ with the zero level (threshold value) the $E_1$ can be equal to V (i.e., $E_1 = V$) when the $E_1$ is more than the zero level and the $E_1$ can be equal to $-V$ (i.e., $E = -V$) when the $E_1$ is less than the zero level. The signal $E_2$ after the waveform conversion is:

$$E_2 = \frac{4V}{\pi} \cos(2\pi F_b t + P(t) + \phi) + \text{(Harmonic wave content)} \qquad (5)$$

As the signal $E_2$ does not include A, the thermal expansion displacement (amplitude L, Phase P) can be accurately measured.

In order to extract the signal component having the frequency $F_b - F$ from the $E_2$, it can be considered that a frequency analyzer, an FM tuber, etc. are utilized. However, when the signal level is low, it is proper that a synchronous detection system is used. In this case, the synchronous detection may be executed with a signal having the frequency $F_b - F$ as reference signal. But as an optical interferometer is generally liable to be influenced by atmospheric swing, disturbance vibrations, etc., they will become noises, thereby causing timelike fluctuation to be brought in the phase $\phi$ in the expressions (2) and (5). The fluctuation of $\phi$ results in fluctuation of V, and the thermal expansion vibrations can not be measured stably.

Hence, in the embodiment, the $E_2$ is firstly multiplied by a fluctuation signal (M.sin ($2\pi F_t + q$) with a multiplicator $14_a$. M and q are the constants that have been already known. After the multiplication, the signal $V_m$ is:

$$V_m = R \cos(2\pi(F_b + F)t + \phi + q) + R \cos(2\pi(F_b - F)t + \phi - q) \qquad (7)$$

($R = 2MV/\pi$)

Then, the signal $V_r$ of the second term in the right side of the above expression is taken out by passing the Vm through a filter 15a. Subsequently, synchronous detection is executed with this $V_r$ utilized as reference signal. In case that the synchronous detection 16a is executed as the Vr utilized as reference signal as the $V_r$ includes the phase $\phi$, the influence of the phase $\phi$ at V is counterbalanced. The synchronous detection output $V_o$ is:

$$V_o = \frac{4V}{\lambda} L\cos(P + q) \quad (8)$$

Therefore, the phase $\phi$ can be eliminated, and $V_o$ can be stably measured, thereby causing the thermal expansion displacement to be accurately measured.

Furthermore, the above description deals with extraction of the frequency $F_b - F$. However, at the $E_2$, the component of the frequency $F_b + F$ also includes information of thermal expansion vibrations. Therefore, the thermal expansion vibrations can be measured by using the signal of the first term in the right side of $V_m$ of the expression (7).

What is claimed is:

1. A method for sample evaluating by measuring thermal expansion displacement on the surface of the sample, which is produced by irradiating the sample with an excitation beam of which intensity is cyclically modulated at a frequency F, comprising the steps of:
    irradiating a surface position of the sample which is subjected to thermal expansion by irradiation of the excitation beam with a measuring beam having an optical frequency F1 to produce a reflection beam;
    interfering said reflection beam with a reference beam having an optical frequency F2;
    photoelectrically converting said interference beam to electric signals E;
    obtaining beat wave signals E1 of the electric signals E having a beat frequency Fb where Fb=F1−F2;
    binarizing the beat wave signals E1 and converting the beat wave signals E1 to binary signals E2 to prevent changes in reflectivity of said sample due to temperature change and plasma density change of said sample from influencing measurement of thermal expansion displacement; and
    extracting components of the frequency Fb−F or Fb+F from the binary signals E2, thereby causing the sample to be evaluated according to the amplitude and phase of the respective component.

2. A method for sample evaluating by measuring thermal expansion displacement on the surface of the sample, which is produced by irradiating the sample with an excitation beam of which intensity is cyclically modulated at a frequency F, comprising the steps of:
    irradiating the surface of the sample which is subjected to thermal expansion by irradiation of the excitation beam with a measuring beam having an optical frequency F1 to produce a reflection beam;
    interfering the reflection beam with a reference beam having an optical frequency F2;
    photoelectrically converting the interference beam to electric signals E;
    obtaining beat wave signals E1 whose beat frequency Fb=F1−F2 from the electric signals E;
    binarizing the beat wave signals E1 and converting the binarized signals to binary signals E2 to prevent changes in reflectivity of said sample due to temperature change and plasma density change of said sample from influencing measurement of thermal expansion displacement;
    creating delay signals Eb, which are delayed from time $\tau$ from the binary signals E2; and
    obtaining a signal Vt by multiplying the binary signals E2 by the delay signals Eb, and extracting a signal component Va regarding the frequency F therefrom, thereby causing the sample to be evaluated according to the amplitude and phase of the signal component Va.

3. A method for sample evaluating by measuring thermal expansion displacement on the surface of the sample, which is produced by irradiating the sample with an excitation beam of which intensity is cyclically modulated at a frequency F, comprising the steps of:
    irradiating the surface of the sample which is subjected to thermal expansion by irradiation of the excitation beam with a measuring beam having an optical frequency F1, in order to produce a reflection beam;
    interfering the reflection beam with a reference beam having an optical frequency F2;
    photoelectrically converting the interference beam to electric signal E;
    obtaining beat wave signals E1 having beat frequency Fb=F1−F2 from electric signals E;
    binarizing the beat wave signals E1 in order to convert the beat wave signals to binary signals E2 to prevent changes in reflectivity of said sample due to temperature change and plasma density change of said sample from influencing measurement of thermal expansion displacement;
    multiplying the binary signals E2 by local oscillating signals Eb of frequency Fb to obtain a signal Vu;
    multiplying a signal E4 whose phase is different by 90° from the signal E2 by the local oscillating signals Eb of frequency Fb to obtain a signal Vn;
    extracting a component Vs of the frequency F from the signal Vu and extracting a component Vc of frequency F from the signals Vn; and
    operating on the components Vs and Vc to produce an output Vo having a variable concerning only the phase change P(t) of the measuring beam on account of the thermal expansion displacement of the sample, whereby the sample is evaluated according to the output Vo.

4. A method for sample evaluating by measuring thermal expansion displacement on the surface of the sample, which is produced by irradiating the sample with an excitation beam of which intensity is cyclically modulated, comprising the steps of:
    irradiating a surface position of the sample which is subjected to thermal expansion by irradiation of the excitation beam with a measuring beam having an optical frequency F1 of which intensity is modulated with the frequency F to produce a reflection beam;
    interfering said reflection beam with a reference beam having an optical frequency F2;
    photoelectrically converting said interference beam to electric signals E;
    obtaining beat wave signals E1 of the electric signals E having a beat frequency Fb where Fb=F1−F2;
    binarizing the beat wave signals E1 and converting the beat wave signals E1 to binary signals E2; and
    extracting components of the frequency Fb−F or Fb+F from the binary signals E2, thereby causing the sample to be evaluated according to the amplitude and phase of the respective component.

5. A method for sample evaluating by measuring thermal expansion displacement on the surface of a sample, which is produced by irradiating thereto an excitation beam of which intensity is cyclically (frequency: F) modulated, comprising the steps of:
    irradiating a measuring beam having an optical frequency F1 of which intensity is modulated with the frequency F to produce a reflection beam;
    interfering said reflection beam with a reference beam having an optical frequency F2;
    photoelectrically converting said interference beam to electric signals E;
    obtaining beat wave signals E1 of electric signals E habign a beat frequency Fb where Fb=F1−F2;
    binarizing the beat wave signals E1 and converting the beat wave signals E1 to binary signals E2;
    creating delay signals Eb which are delayed by time τ from said binary signals E2; and
    obtaining a signal Vt by multiplying the binary signals E2 by the delay signals Eb, and extracting a signal component Va regarding the frequency F therefrom, thereby causing the sample to be evaluated according to the amplitude and phase of the signal component Va.

6. A method for sample evaluating by measuring thermal expansion displacement on the surface of a sample, which is produced by irradiating the sample with an excitation beam of which intensity is cyclically (frequency: F) modulated, comprising the steps of:
    irradiating a measuring beam having an optical frequency F1 of which intensity is modulated with the frequency F to produce a reflection beam;
    interfering said reflection beam with a reference beam having an optical frequency F2;
    photoelectrically converting the interference beam to electric signals E;
    obtaining beat wave signals E1 of the electric signals E having a beat frequency Fb where Fb=F1−F2;
    binarizing the beat wave signals E1 and converting the beat wave signals E1 to binary signals E2;
    multiplying the binary signals E2 by local oscillating signals Eb of frequency Fb to obtain a signal Vu;
    multiplying a signal E4 whose phase is different by 90° from the signal E2 by the local oscillating signals Eb of frequency Fb to obtain a signal Vn;
    extracting a component Vs of the frequency F from the signal Vu and extracting a component Vc of frequency F from the signals Vn; and
    operating on the components Vs and Vc to produce an output Vo having a variable concerning only the phase change P(t) of the measuring beam on account of the thermal expansion displacement of the sample, whereby the sample is evaluated according to the output Vo.

* * * * *

UNITED STATES PATENT AND TRADEMARK OFFICE
CERTIFICATE OF CORRECTION

PATENT NO. : 5,298,970
DATED : March 29, 1994
INVENTOR(S) : Hiroyuki TAKAMATSU, et al.

It is certified that error appears in the above-indentified patent and that said Letters Patent is hereby corrected as shown below:

On the title page, Item [54] and Column 1, Line 2, the title should read as follows:

--SAMPLE EVALUATING METHOD USING INTERFEROMETRIC TECHNIQUES TO EVALUATE LASER INDUCED THERMAL EXPANSION DISPLACEMENT OF A SAMPLE--

On the title page, item (30): The first Foreign Application Priority Data should read as follows:

--Mar. 20, 1990 [JP] Japan ............... 2-70967--

Signed and Sealed this

Ninth Day of August, 1994

Attest:

Attesting Officer

BRUCE LEHMAN

Commissioner of Patents and Trademarks